United States Patent [19]
Gale et al.

[11] Patent Number: 5,840,327
[45] Date of Patent: Nov. 24, 1998

[54] TRANSDERMAL DRUG DELIVERY DEVICE HAVING ENHANCED ADHESION

[75] Inventors: Robert M. Gale, Los Altos; Patricia S. Campbell, Palo Alto, both of Calif.

[73] Assignee: ALZA Corporation, Palo Alto, Calif.

[21] Appl. No.: 704,426

[22] Filed: Aug. 15, 1996

Related U.S. Application Data

[60] Provisional application No. 60/002,576 Aug. 21, 1995.
[51] Int. Cl.$^6$ ........................................... A61F 13/02
[52] U.S. Cl. ........................... 424/448; 424/447; 424/449
[58] Field of Search .................................. 424/447, 448, 424/449

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |
| 4,286,592 | 9/1981 | Chandrasekaran | 128/260 |
| 4,314,557 | 2/1982 | Chandrasekaran | 128/260 |
| 4,379,454 | 4/1983 | Campbell et al. | 604/897 |
| 4,435,180 | 3/1984 | Leeper | 604/896 |
| 4,559,222 | 12/1985 | Enscore et al. | 424/28 |
| 4,568,343 | 2/1986 | Leeper et al. | 604/896 |
| 4,573,999 | 3/1986 | Netto | 623/7 |
| 4,588,580 | 5/1986 | Gale et al. | 424/21 |
| 4,645,502 | 2/1987 | Gale et al. | 604/896 |
| 4,661,099 | 4/1987 | Von Bittera | 604/290 |
| 4,699,792 | 10/1987 | Nick et al. | 424/446 |
| 4,704,282 | 11/1987 | Campbell et al. | 424/449 |
| 4,711,781 | 12/1987 | Nick et al. | 424/446 |
| 4,725,439 | 2/1988 | Campbell et al. | 424/449 |
| 4,743,249 | 5/1988 | Loveland | 424/447 |
| 4,816,258 | 3/1989 | Nedberge et al. | 424/448 |
| 4,849,226 | 7/1989 | Gale | 424/448 |
| 4,867,982 | 9/1989 | Campbell et al. | 424/449 |
| 4,904,475 | 2/1990 | Gale et al. | 424/448 |
| 4,908,027 | 3/1990 | Enscore et al. | 604/890.1 |
| 4,938,759 | 7/1990 | Enscore et al. | 604/896.1 |
| 4,943,435 | 7/1990 | Baker et al. | 424/448 |
| 5,004,610 | 4/1991 | Osborne et al. | 424/448 |
| 5,132,115 | 7/1992 | Wolter et al. | 424/448 |
| 5,462,743 | 10/1995 | Turner | 424/448 |

FOREIGN PATENT DOCUMENTS

| | | | |
|---|---|---|---|
| 0 571 264 A1 | 11/1993 | European Pat. Off. | A61K 31/505 |

OTHER PUBLICATIONS

Black "Transdermal Drug Delivery Systems", US Pharmacist, Nov. 1982, pp. 49–78.

Arita, et al., "Studies on Percutaneous Absorption of Drugs", Chem. Phar. Bull., vol. 18, 1970, pp. 1045–1049.

Idson, "Percutaneous Absorption", J. Phar. Sci., vol. 64, No. 6, pp. 910–922, 1975.

Clooney, Advances in Biomedical Engineering, Part 1, Chapter 6, "Drug Permeation Through Skin: Controlled delivery for Topical or Systemic Therapy", Marcel Dekker, Inc., New York, and Basel, 1980, pp. 305–318.

J. DeBoever et al., Variation of Progesterone, 20 α–Dihydroprogesterone and Oestradiol Concentration in Human Mammary Tissue and Blood after Topical Administration of Progesterone, Percutaneous Absorption of Steroids, Academic Press, New York, pp. 259–265 (1980).

R. Sitruk–Ware et al., Treatment of Benign Breast Diseases by Progesterone Applied Topically, pp. 219–229, Percutaneous Absorption of Steroids, Academic Press, New York, (1980).

Chandrasekaran, Advances in Biomedical Engineering, Part 1, Chapter 6, "Drug Permeation Through Skin: Controlled delivery for Topical or Systemic Therapy", Marcel Dekker, Inc., New York and Basel, 1980, pp. 305–318.

*Primary Examiner*—D. Gabrielle Brouillette
*Attorney, Agent, or Firm*—Michael J. Rafa; Steve F. Stone

[57] ABSTRACT

A device for the transdermal administration of a drug to a sensitive body area such as the scrotum. Devices according to the invention provide an improved quality of adhesion to the body area while also providing patient comfort during use and upon removal of the device. Also disclosed are methods of transdermal delivery such as the transcrotal delivery of testosterone to hypogonadic males.

12 Claims, 2 Drawing Sheets

TRANSDERMAL DRUG DELIVERY DEVICE HAVING ENHANCED ADHESION

This application claims benefit to Provisional Application No. 60/002,576, filed Aug. 21, 1995.

FIELD OF INVENTION

This invention relates to medical devices for delivering drugs to the body through intact skin and more particularly to the delivery of drugs at therapeutically effective rates through sensitive areas of intact skin. The transdermal devices of this invention provide improved quality of adhesion of the device to sensitive body areas such as the scrotum.

BACKGROUND OF THE INVENTION

The transdermal route of parenteral delivery of drugs provides many advantages, and transdermal systems for delivering a wide variety of drugs or other beneficial agents are described in U.S. Pat. Nos. 3,598,122; 3,598,123; 3,731,683; 3,797,494; 4,286,592; 4,314,557; 4,379,454; 4,435,180; 4,559,222; 4,568,343; 4,573,999; 4,588,580; 4,645,502; 4,704,282; 4,816,258; 4,849,226; 4,908,027; 4,938,759; 4,943,435; and 5,004,610, for example, all of which are incorporated herein by reference.

The site of administration of transdermal delivery devices has been selected at various locations such as behind the ear, on the chest, or on the thigh for various reasons such as desired skin permeability to an agent, convenience, or cosmetic reasons. It has been known for some time that permeability of human skin varies from site to site and that scrotal skin tends to have a higher permeability than other skin.

Devices adapted to deliver drug through scrotal skin are known in the art as disclosed in U.S. Pat. Nos. 4,704,282, 4,725,439, and 4,867,982, for example, which are herein incorporated in their entirety by reference. These devices utilize a skin contacting surface comprising a drug, such as testosterone, dispersed in a tacky ethylene vinyl acetate (EVA) carrier that non-adhesively maintains the device in a skin contacting relation. However, the non-adhesive tack of the EVA carrier has been found to be insufficient in some patients to maintain these systems in skin contacting relation throughout a desired administration time of about 24 hours.

The shape and texture of scrotal skin require a highly flexible device possessing a certain amount of compliance or non-elastic stretch in order to be capable of comfortably conforming to the wrinkles, folds, and irregular shape of scrotal skin in agent transmitting relationship thereto and thereafter remain in this slightly deformed condition rather than returning to its original configuration. Patient discomfort is a crucial factor in patient compliance, and that comfort depends not only on flexibility and stretchability of the device while being worn, but also on sensations attendant to removal. Securement methods such as typical contact adhesives, belts, buckles, tapes, and elastic bands have all been found to be unacceptably uncomfortable.

Transdermal drug delivery devices having patterned or discontinuous adhesive skin contacting areas are also known in the art. For example, U.S. Pat. No. 4,699,792 discloses a transdermal device with cap shaped adhesive elements and medicinal active ingredient elements located on a carrier web in a spatially separated arrangement such that there is no interaction between the medicated active ingredient and adhesive.

U.S. Pat. No. 4,711,781 discloses a transdermal device comprising a carrier web with a continuous adhesive coating and a plurality of non-permeable separating film elements spaced from each other on the coating in a pattern. A drug is contained within the perimeter of the separators in order to isolate the drug from the adhesive.

U.S. Pat. No. 4,743,249 discloses transdermal patches having a discontinuous pattern printed adhesive layer on the skin-contacting surface of an active-agent porous membrane.

U.S. Pat. No. 4,904,475 describes a porous support structure for use in a device for delivering ionized drugs from an aqueous reservoir.

U.S. Pat. No. 5,132,115 discloses a transdermal therapeutic system comprising a skin contacting area which has one or more non-adhesive drug releasing section(s) and one or more skin-adhesion section(s) which may also contain a drug. The drug-releasing section(s) and the skin-adhesion section(s) are co-planar in order to provide for simultaneous contact with the skin.

In addition, Black "Transdermal Drug Delivery Systems", US Pharmacist, Nov. 1982, pp 49–78, provides additional background information regarding commercially available transdermal drug delivery systems. A reasonably complete summary of the factors involved in percutaneous absorbtion of drugs may be found in Arita, et al, "Studies on Percutaneous Absorption of Drugs", Chem. Phar. Bull., Vol. 18, 1970, pp 1045–1049; Idson, "Percutaneous Absorption", J. Phar. Sci., Vol. 64, No. 6, pp 910–922; and Clooney, Advances in Biomedical Engineering Part I, Chapter 6, "Drug Permeation Through Skin: Controlled Delivery For Topical or Systemic Therapy", Marcel Dekker, Inc., New York and Basel, 1980, pp 305–318.

It has been proposed to gently heat, as with a light bulb or hair dryer, the non-adhesive prior art devices of the type disclosed in U.S. Pat. Nos. 4,704,282, 4,725,439, and 4,867,982 prior to use in order to increase the tack. This results in an undesirable additional step that adversely effects patient compliance and, if avoided, contact efficiency of these systems as the devices tend to fall off if not adequately heat-treated. Further, this preparation step may discourage patients from use of such a system.

Although the transdermal drug delivery route is rapidly becoming a preferred delivery route for a wide variety of drugs, transdermal delivery is not without its problems. While offering encouraging permeabilities to various agents, the sensitivity of scrotal, penile, labial, and mammary skin and their sometimes irregular and changing configurations imposes significant constraints on the characteristics of a delivery device designed for application to these areas. Such a device must be sufficiently thin, flexible, and stretchable so as to easily conform to the site of application and stay in skin contact in a manner which does not create discomfort on removal.

DISCLOSURE OF THE INVENTION

It is accordingly an aspect of this invention to provide a drug delivery device suitable for application to sensitive body sites such as the scrotum, labia, penis, and breast, which device provides enhanced adhesion to these body sites without causing unacceptable discomfort to a patient.

It is another aspect of this invention to provide a transdermal drug delivery device having enhanced adhesion which is suitable for application to sensitive body surfaces and provides therapeutically effective drug delivery rates.

It is another aspect of this invention to provide a transdermal drug delivery device having enhanced adhesion which is suitable for application to sensitive body surfaces which does not require additional preparation prior to application.

It is another aspect of this invention to provide a transdermal drug delivery device having enhanced adhesion which provides an in vivo transdermal administration profile that is a bioequivalent of the in vivo administration profile from a system without enhanced adhesion.

It is another aspect of this invention to provide a transdermal drug delivery device particularly adapted for scrotal delivery of at least one drug through intact scrotal skin.

It is yet another aspect of this invention to deliver testosterone by transcrotal delivery from a device having enhanced adhesion.

These and other objects and advantages of this invention will be readily apparent from the following description with reference to the accompanying figures.

DETAILED DESCRIPTION OF THE INVENTION

As used herein, the term "drug" is to be construed in its broadest sense as material which is intended to produce some beneficial effect on the organism to which it is applied.

As used herein, the term "transdermal" delivery or application refers to the delivery or application of agents by passage of skin, mucosa, and/or other body surfaces by topical application.

As used herein, the term "therapeutically effective" amount or rate refers to the amount or rate of drug or active agent needed to effect the desired therapeutic result.

As used herein, the term "bioequivalent" administration profile refers to a drug delivery profile which remains within ±20% of a reference administration profile.

This invention provides an improved transdermal drug delivery device having enhanced adhesion suitable for application to sensitive body areas such as the scrotum. Devices of this invention provide improved quality of adhesion at the skin contacting surface of the device while also providing patient comfortability during use and upon removal of the device. Additionally, devices of this invention do not necessitate pretreatment with a heat source prior to application. This is accomplished by providing a small percentage of the surface area of the non-adhesive, tacky skin contacting surface of a transdermal drug delivery device such as that disclosed in U.S. Pat. No. 4,725,439 cited above with a suitable adhesive. Surprisingly, the use of an adhesive on the skin contacting surface of a device intended for application to a sensitive body area, such as the scrotum, has been found to provide satisfactory patient comfort while also providing therapeutically effective drug delivery rates.

Figure 1:
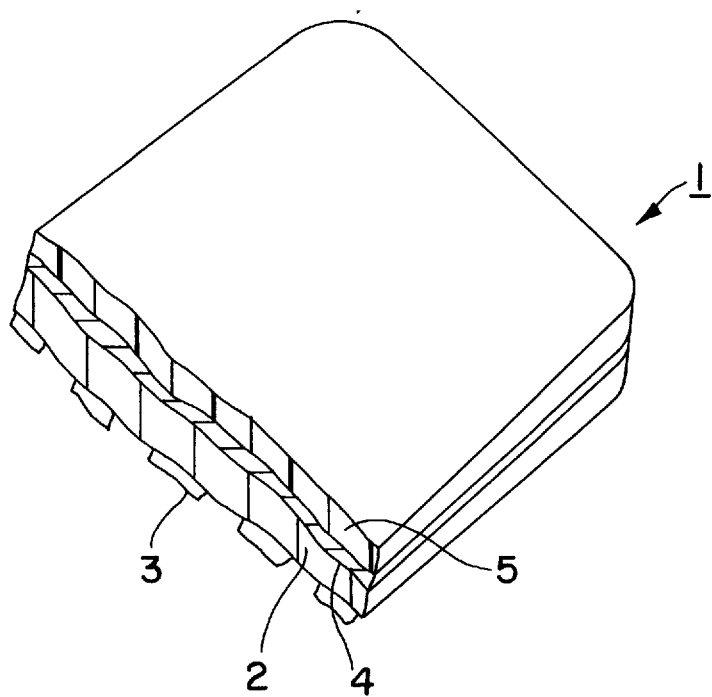
FIG. 1 is a cross-sectional view of one embodiment of the transdermal drug delivery system according to this invention.
Figure 2:
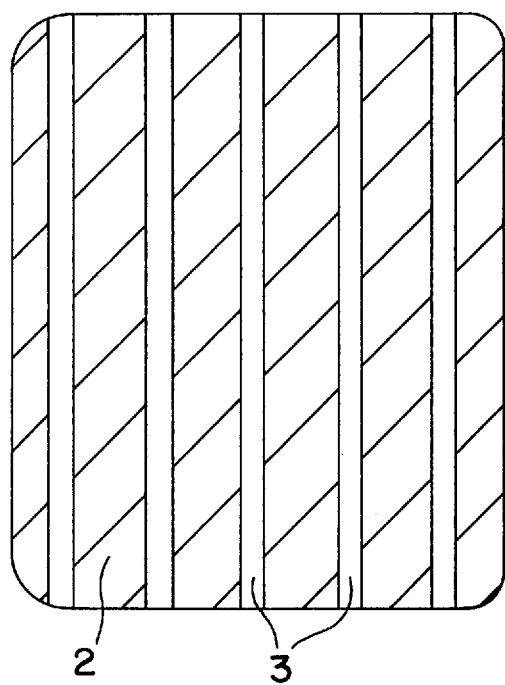
FIG. 2 is a bottom view of a drug delivery system according to this invention absent a release liner.

Referring now to FIG. 1, a preferred embodiment of a transdermal delivery device 1, according to this invention is shown. The system is specifically adapted to increase the quality of adhesion at the skin-facing, drug transfer surface of drug reservoir 2. In FIG. 1, transdermal delivery device 1, comprises a reservoir 2 in the form of a non-aqueous polymeric carrier having the agent to be delivered dissolved or dispersed therein, which carrier has a viscosity and strength sufficient to enable the device to maintain its structural integrity during use without flowing, oozing, or otherwise disintegrating. The carrier has a limited amount of tack which allows it to cling to the skin to which it is attached. In addition, the carrier may also contain skin permeation enhancers, dies, pigments, inert fillers, stabilizing agents, excipients, and other conventional components of pharmaceutical products for transdermal devices known in the art.

In order to improve the quality of adhesion of reservoir 2 to a patient's skin while maintaining a satisfactory level of patient comfortability and therapeutically effective drug delivery rates, adhesive 3 is provided in a pattern on the skin-facing surface of reservoir 2. The adhesive is preferably provided as a parallel repeating pattern of stripes positioned lengthwise along the skin-facing surface of reservoir 2 and laminated thereto. Other patterns such as dots or a checkerboard may be used and other means, such as pattern printing, may be utilized to provide the surface of reservoir 2 with the adhesive in virtually any pattern. The total surface area of adhesive on the skin-facing surface must be selected such that the resultant adhesive bond with the skin is sufficient to maintain skin contact throughout the desired administration period and not cause discomfort to the patient during use and upon removal, while providing therapeutically effective drug delivery rates.

The body distal surface is provided with reinforcing means 5, typically in the form of a nonwoven, woven, or knit, relatively open mesh fabric that is chemically inert with respect to other components of the system, in order to strengthen the reservoir 2, facilitate handling, application, and removal of the device, and provide a textured feel to the body distal surface. Reinforcing means 5 is bonded to the device, embedded either in the upper surface of reservoir 2 or in a discrete layer of bonding agent 4 having characteristics different from those of the carrier forming reservoir 2. Reinforcing means 5 and bonding layer 4 are more fully described in U.S. Pat. No. 4,725,439 cited above. A strippable release liner (not shown in FIG. 1) is normally provided along the exposed skin contacting surface and removed prior to application of device 1 to the skin.

The purpose of the patterned adhesive is to improve the adhesion of the device to the skin but not to affect the comfortability or the transdermal administration profile of the drug from therapeutic transdermal systems without the adhesive. The in vivo drug administration profiles from devices of this invention are preferably bioequivalent to the drug administration profiles from devices without adhesive. The decline in in vitro drug release rates attributed to the the low permability of drug through the adhesive may be compensated for by the improved in vivo contact efficiency. For example, a therapeutic transdermal system containing testosterone according to this invention should provide maximum serum testosterone concentrations of about 600 ng/dL at 2–4 hours post-application before gradually declining to about 300 ng/dL after about 22 hours application. Suitable adhesives include, but are not limited to, silicone polymers, acrylate polymers, polyisobutylene (PIB) adhesives, and styrene-isoprene copolymers with tackifier (s). PIB adhesives are preferred.

The permeability of drug through the adhesive is usually substantially lower than that through the reservoir material. PIB adhesives, for example, are only slightly permeable to testosterone. In vitro drug release rates from systems according to this invention will vary with the thickness of the adhesive in addition to the total surface area of the adhesive pattern. Additionally, the adhesive width has a significant effect on the peel strength of the adhesive. Thus, there are significant constraints imposed upon the design characteristics of the adhesive pattern.

The adhesive pattern is selected, in part, by providing that the adhesive pattern covers a small percentage of the total skin-facing surface area of the reservoir 2. In a preferred embodiment, reservoir 2 is provided with a small number of adhesive stripes, preferably 1–10, which cover less than 20%, more preferably 5–18%, most preferably 8–16%, of the total surface area of the reservoir 2. The width of the stripes is preferably within the range of about 0.5–5.0 mm and the stripe thickness preferably varies from about 0.2–1.5 mils. In a particularly preferred embodiment, the system is provided with 5 longitudinally arranged, parallel stripes of a PIB adhesive having a width of about 1.5 mm, a thickness of about 1 mil (0.001 inch), and spaced apart approximately every 12.7 mm.

Suitable carriers for reservoir 12 can be selected from a variety of materials known to the art, provided they possess the required compatibility with the agent, structural strength, flexibility, and tackiness. As noted in the U.S. Patents cited above, such material include without limitation, tacky natural and synthetic polymers and blends such as natural or synthetic rubbers, and ethylene vinylacetate (EVA) copolymers such as are disclosed for example in U.S. Pat. Nos. 4,069,307 and 4,144,317, which are incorporated herein by reference. EVA polymers having a vinyl acetate (VA) content of from about 28–61% and preferably about 40–60% possess characteristics of solubility, permeability, and tack to be suitable for the delivery of a wide variety of agents according to this invention.

Although any agent which is suitable for transdermal administration can be delivered according to this invention, certain agents are particularly suited for administration from devices according to this invention. Testosterone constitutes a preferred agent for delivery according to this invention, particularly for use in the treatment of hypogonadic males. Other preferred agents include estradiol, which can be administered to the labia for treatment of postmenopausal disorder for example, and progesterone which can be administered to the breast to correct estrogen-progesterone imbalance in women with benign breast disease as suggested by J. DeBoever et al., *Variation of Progesterone, 20 α-Dihydroprogesterone and Oestradiol Concentration in Human Mammary Tissue and Blood After Topical Administration of Progesterone,* Percutaneous Absorption of Steroids, Academic Press, New York, pp. 259–265 (1980) and R. Sitruk-Ware et al., *Treatment of Benign Breast Diseases by Progesterone Applied Topically,* Ibid., pp. 219–229.

The amount of drug present in the therapeutic device and required to achieve an effective therapeutic result depends on many factors, such as the minimum necessary dosage of the drug of the particular indication being treated; the solubility and permeability of the carrier and adhesive layer; and the period of time for which the device will be fixed to the skin. The minimum amount of drug is determined by the requirement that sufficient quantities of drug must be present in the device to maintain the desired rate of release over the given period of application. The maximum amount for safety purposes is determined by the requirement that the quantity of drug present cannot exceed a rate of release that reaches toxic levels. Generally, the maximum concentration is determined by the amount of agent that can be received in the carrier without producing adverse histological effects such as irritation, an unacceptably high initial pulse of agent into the body, or adverse effects on the characteristics of the delivery device such as the loss of tackiness, viscosity, or deterioration of other properties.

The initial loading of agent in the carrier will determine the useful life of the device, typically from 8 hours to seven days. The invention can be used for such time periods, however, certain preferred embodiments are particularly adapted for administration periods of up to about 24 hours. The drug may be present in the carrier at a concentration in excess of saturation, the amount of excess being a function of the desired length of the drug delivery period of the system. The drug may, however, be present at a level below saturation without departing from this invention as long as the drug is continuously administered to the skin or mucosal site in an amount and for a period of time sufficient to provide the desired therapeutic rate. For example, the release rate tends to decline more rapidly with time of use from subsaturated systems than from saturated systems, thus subsaturated systems are particularly useful with hormones such as testosterone where circadian variations in blood level is normal.

The surface area of the device of this invention can vary from about 15 $cm^2$ to about 75 $cm^2$. A typical device, however, will have a surface area within the range of about 20–60 $cm^2$. A typical transcrotal device is fabricated as an approximately 60 $cm^2$ generally elliptical or rectangular patch with rounded corners. The patches are intended to be applied and left in place preferably while wearing close fitting clothing such as jock straps or jockey shorts, panties, or brassieres, for example, to protect the device from unnecessary physical contact or motion and assist in maintaining the device in contact with the skin for the desired period.

The devices of this invention can be designed to effectively deliver drug for an extended period of time from several hours up to seven days or longer. Seven days is generally the maximum time limit for application of a single device because the adverse effect of inclusion of a skin site increases with time and a normal cycle of sloughing and replacement of the skin cells occurs in about seven days.

The aforementioned patents describe a wide variety of materials which can be used for fabricating the various layers and components of the transdermal drug delivery devices according to this invention. This invention, therefore, contemplates the use of materials other than those specifically disclosed herein, including those which may hereafter become known to the art and to be capable of performing the necessary functions.

The following examples are offered to illustrate the practice of the present invention and are not intended to limit the invention in any manner.

EXAMPLE 1

The drug reservoir was prepared by mixing ethylene vinyl acetate copolymer having a vinyl acetate content of 40 percent ("EVA 40", U.S.I. Chemicals, Ill.) in an internal mixer (Bra Bender type mixer) until the EVA 40 pellets fused. Testosterone was then added to the internal mixing bowl to generate a 2 wt % blend. The mix was extruded onto a fluorocarbon coated polyester release liner available from 3M Co. After production, a reservoir of 12.5 mg/$cm^2$ containing 0.25 mg testosterone per $cm^2$ was fabricated. The testosterone reservoir was then laminated to a spun laced polyester backing (Sontara®, DuPont, Wilmington, Del.) and die-cut to 60 $cm^2$ systems using a Mark Andy rotary die-cutting/laminating machine.

Stripes of polyisobutylene adhesive positioned between two release liners were obtained (Mactac Co. Scranton, Pa.) as a roll with PIB stripes approximately 2 mm in width with a repeat at approximately every 13.5 mm. To study the functionallity of the number of adhesive stripes with the release rate, zero—five PIB stripes were manually transferred to the testosterone reservoir with equal spacing.

The release liner of the laminate was removed and the system was then mounted on a Teflon® rod. A known volume of receptor solution (0.10% phenol/H$_2$O) was then placed in a test tube and was equilibrated at 35° C. The Teflon rod with the attached system was then placed in a water bath at 35° C. Mixing was accomplished by attachment to a motor which caused constant vertical mixing.

Figure 3:
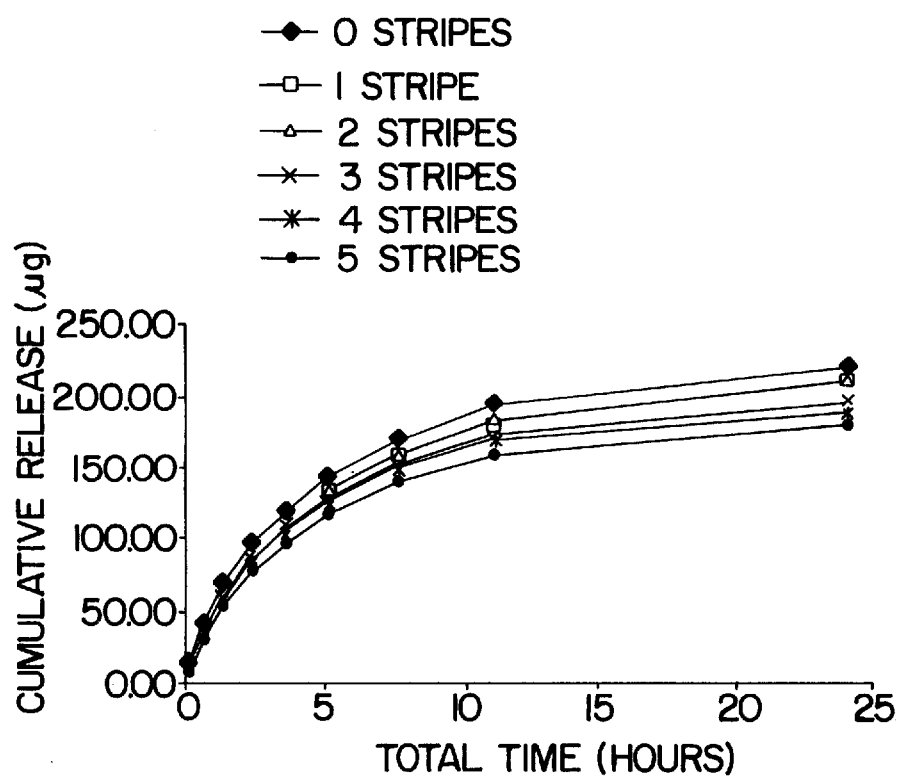
FIG. 3 is a graph showing the cumulative release of testosterone as a function of added adhesive stripes.

At given time intervals, the entire receptor solution was removed from the test tubes and replaced with an equal volume of fresh receptor solutions previously equilibrated at 35° C. The receptor solutions were stored in capped vials at 4° C. until assayed for testosterone content by HPLC. The release of testosterone as a function of added adhesive stripes is shown in FIG. 3.

EXAMPLE 2

Drug reservoirs comprising 2 wt % testosterone and 98 wt % EVA were prepared as set forth in Example 1. Five PIB stripes each having a width of 1.5 mm and a thickness of about 1 mil were laminated to some of the drug reservoirs. Approximately 5 wt % of colloidal silicon dioxide (Cabosil®, Boston, Mass.) was added to the stripes prior to lamination in order to prevent the stripes from spreading after lamination to the reservoir. The PIB stripes were laminated longitudinally to the testosterone reservoir at ambient temperature using a Mark Andy rotary die-cutting/laminating machine. The stripes were arranged lengthwise on the testosterone releasing surface and spaced apart approximately every 12.7 mm.

A strip having a 6.6 cm length and 1.45 cm width was then cut across the system perpendicular to the stripes. This strip was then mounted on a metal cylinder and held in place with a nylon net and viton o-rings. A known volume of receptor solution (0.10% phenol/H$_2$O) was then placed in a beaker and was equilibrated at 35° C. The assembly with the attached system was then placed in a water bath at 35° C. Mixing was accomplished by attachment to a motor which caused constant vertical mixing.

At given time intervals, the entire receptor solution was removed from the beaker and replaced with an equal volume of fresh receptor solutions previously equilibrated at 35° C. The receptor solutions were stored in capped vials at 4° C. until assayed for testosterone content by HPLC. From the drug concentration and the volume of the receptor solutions, the area of permeation and the time interval, the flux of the drug was calculated as follows: (drug concentration X volume of receptor)/(area×time)=flux ($\mu$g/cm$^2$•hr). The average testosterone flux throughout three segments of a 24 hour period and the total testosterone release from the 60 cm$^2$ system over the 24 hour period are shown in Table 1 below. As seen in Table 1, both systems with and without adhesive stripes effectively deliver testosterone at a pattern approximating the normal circadian testosterone pattern.

TABLE 1

Testosterone in vitro Flux and Total Release
For Systems With and Without Adhesive Stripes

| SYSTEM | FLUX ($\mu$g/cm$^2$ · hr) | | | TOTAL RELEASED |
|---|---|---|---|---|
| | 0–4 hr | 4–12 hr | 12–24 hr | 60 cm$^2$ system (mg) |
| with stripes | 29.07 | 7.44 | 1.90 | 12.05 |
| no stripes | 35.88 | 8.46 | 1.76 | 14.10 |

EXAMPLE 3

The flux of testosterone through systems using PIB stripes of varying width and thickness was evaluated. Drug reservoirs were prepared as set forth in Example 1. Five stripes of PIB adhesive were positioned lengthwise and spaced apart equally along the testosterone releasing surface of the system and laminated thereto as described in Example 2. The stripes were either 2.5–3 mm wide and approximately 0.6 mils thick (thin stripes) or 1.5 mm wide and about 1 mil thick (thick stripes). The flux experiment described in Example 2 was repeated using these systems. The testosterone flux and total testosterone release from systems with stripes of varying geometry are shown in Table 2.

TABLE 2

Testosterone in vitro Flux and Total
Release For Systems With Adhesive Stripes

| SYSTEM | FLUX ($\mu$g/cm$^2$ · hr) | | | TOTAL RELEASED |
|---|---|---|---|---|
| | 0–4 hr | 4–12 hr | 12–24 hr | 60 cm$^2$ system (mg) |
| thick stripes | 23.3 | 6.7 | 2.1 | 11.1 |
| thin stripes | 25.5 | 6.5 | 1.6 | 11.3 |

EXAMPLE 4

Systems were prepared according to Example 2. The in vitro flux experiment of Example 2 was repeated using an EVA membrane having a 9% vinyl acetate content and a thickness of 2 mil to simulate scrotal skin in order to measure the testosterone flux through the EVA membrane for systems with and without adhesive. The membrane exhibits characteristics approximating scrotal skin and is useful for predicting in vivo flux through scrotal skin. Results are shown in Table 3. As seen in Table 3, the flux was consistently greater from systems with PIB stripes than from systems without adhesive stripes and the total testosterone release for the systems with enhanced adhesion exceeded that from the systems without adhesive. As seen in Table 3, all of the testosterone flux values and the total testosterone release for the systems with and without adhesive are within ±20% of each other.

TABLE 3

Testosterone in vitro Flux and Total Release Through an
EVA Membrane (9% VA content, 2 mil thickness) For Systems
With and Without Adhesive

| SYSTEM | FLUX ($\mu$g/cm$^2$ · hr) | | | TOTAL RELEASED |
|---|---|---|---|---|
| | 0–4 hr | 4–12 hr | 12–24 hr | 60 cm$^2$ system (mg) |
| with stripes | 4.00 | 2.75 | 2.20 | 3.80 |
| no stripes | 3.60 | 2.50 | 2.10 | 3.60 |

EXAMPLE 5

The adhesion of systems with and without PIB stripes was evaluated using systems prepared according to Example 2. A leader strip comprised of polyethylene terephthalate release liner and a strip of silicone based adhesive Polyken tape (Kendall Co.) was attached to the test system by applying the adhesive tape strip to the adhesive face of the test system along the width of the system. The test system had a width of about 2⅝". The skin-contacting surface of the system was then adhered to a stainless steel plate using a standard roller to roll over the system three times without applying any downward pressure. The system remained adhered to the plate for 15–20 minutes before the adhesion test. The plate was then clamped vertically to the lower jaw of an Instron tensile tester (Model 1122) with the leader strip pointing down. The free end of the leader strip was then clamped to the upper jaw of the tensile tester so that the peeling angle was 180°. The system was then peeled from the plate at a 180 degree angle at 200 mm/min. The procedure was repeated using four systems with PIB stripes and four systems without PIB stripes. The average adhesive force of these systems is shown in Table 4. The adhesion is expressed as g/system width due to the non-uniform arrangement of adhesive along the surface of the systems with PIB stripes.

TABLE 4

Adhesive Force of Systems
With and Without PIB Adhesive Stripes (g/system width)

| SYSTEM | ADHESIVE FORCE |
| --- | --- |
| with PIB stripes | 205 +/− 23 |
| without PIB stripes | 50 +/− 2 |

The invention has been described in detail with particular reference to certain preferred embodiments thereof, but it will be understood that variations and modifications can be affected within the scope and spirit of the invention.

What is claimed is:

1. A flexible and compliant device for the transdermal administration of a drug at a therapeutically effective rate through intact skin at sensitive body areas comprising:
    a) a reservoir comprising a drug selected from the group consisting of testosterone, estradiol, and progesterone dispersed throughout a non-adhesive, polymeric carrier permeable to said drug, said reservoir having a skin-facing drug transfer surface and a skin-distal surface;
    b) a discontinuous pattern of adhesive on the skin-facing surface of the reservoir, said adhesive covering about 8–16% of the surface area of said reservoir skin-facing surface, said pattern of adhesive having a skin-adhesion surface that lies in a different plane from that of said reservoir skin-facing drug transfer surface; and
    c) a backing on the skin distal surface of the reservoir.

2. A device according to claim 1 wherein said polymeric carrier comprises an ethylene vinyl acetate copolymer having a vinyl acetate content of 40%.

3. A device according to claim 2 wherein the adhesive is a polyisobutylene adhesive.

4. A device according to claim 1 wherein the discontinuous pattern of adhesive covers about 12% of the surface area of said reservoir skin-facing surface.

5. A device according to claim 4 wherein said discontinuous pattern comprises 1–8 parallel, longitudinal stripes of adhesive separated a predetermined distance from each other.

6. A device according to claim 5 wherein said pattern comprises 5 stripes of adhesive and said predetermined distance is about 1.27 cm.

7. A flexible and compliant device for the transdermal administration of testosterone at a therapeutically effective rate through intact scrotal skin comprising:
    a) a reservoir comprising testosterone dispersed throughout a non-adhesive, polymeric carrier permeable to said testosterone, said reservoir having a skin-contacting surface and a skin-distal surface;
    b) a discontinuous pattern of adhesive on the skin-contacting surface of the reservoir, said adhesive covering about 8–16% of the surface area of said reservoir skin-contacting surface, said pattern of adhesive having a skin-contacting surface that lies in a different plane from that of said reservoir skin-contacting surface; and
    c) a backing on the skin distal surface of the reservoir.

8. A device according to claim 7 wherein said polymeric carrier comprises an ethylene vinyl acetate copolymer having a vinyl acetate content of 40%.

9. A device according to claim 8 wherein the adhesive is a polyisobutylene adhesive.

10. A device according to claim 7 wherein the discontinuous pattern of adhesive covers about 12% of the surface area of said reservoir skin-facing surface.

11. A device according to claim 10 wherein said discontinuous pattern comprises 1–8 parallel, longitudinal stripes of adhesive separated a predetermined distance from each other.

12. A device according to claim 11 wherein said pattern comprises 5 stripes of adhesive and said predetermined distance is about 1.27 cm.

* * * * *